United States Patent [19]

Holloway, Jr. et al.

[11] Patent Number: 5,543,330

[45] Date of Patent: Aug. 6, 1996

[54] METHOD FOR DIAGNOSING MYOFIBROGRANULOMA (MFG) IN WALLEYE

[75] Inventors: Harry L. Holloway, Jr., Grand Forks; Craig A. Shoemaker, Stanley, both of N. Dak.

[73] Assignee: Center for Innovation & Business Development Foundation, Grand Forks, N. Dak.

[21] Appl. No.: 532,091

[22] Filed: Sep. 22, 1995

[51] Int. Cl.$^6$ ............................ G01N 33/20; G01N 33/12
[52] U.S. Cl. ................. 436/79; 436/63; 436/98; 436/811; 119/216
[58] Field of Search ................................ 436/63, 79, 98, 436/811; 119/215, 216, 217

[56] References Cited

PUBLICATIONS

DISCRIM & STEPDISC procedures: SAS Institute Inc. 1985. *SAS User's Guide: Statistics*, Version 5 edition. SAS Institute, Inc., Cary, North Carolina.

*Primary Examiner*—Lyle A. Alexander
*Attorney, Agent, or Firm*—Zarley, McKee, Thomte, Voorhees, & Sease

[57] ABSTRACT

An improved method for diagnosing myofibrogranuloma (MFG) in walleye without harming the fish is described. Blood samples are drawn from walleye and creatinine and calcium levels are then determined along with the sex and length of the fish. These data are then analyzed and compared to data from healthy walleye using discriminant analysis. The process is effective for identifying approximately 88% of MFG-positive walleye.

12 Claims, 2 Drawing Sheets

METHOD FOR DIAGNOSING MYOFIBROGRANULOMA (MFG) IN WALLEYE

FIELD OF THE INVENTION

The present invention relates to methods to diagnose disease, in particular, a method for diagnosing myofibrogranuloma (MFG) in walleye.

BACKGROUND OF THE INVENTION

Myofibrogranuloma (MFG) is a degenerative disease of skeletal muscle recognized only in walleye (*Stizostedion vitreum*). MFG is a unique form of skeletal degeneration. The disease is characterized by profound alterations of the trunk musculature produced by extensive hypertrophy of the muscle fibers. Two degenerative processes are involved. The first and most pronounced lesion consists of coagulation necrosis of muscle fibers accompanied by an inflammatory response and formation of granulomas (muscle tumors). The second is non-inflammatory and characterized by local areas of acute myolysis. Opaque, yellowish brown muscle with a sandy texture is seen in fish with advanced forms of the myopathy. Fishermen will usually discard fish with advanced MFG because the lateral trunk muscles (fillet) especially beneath the skin becomes sandy, discolored and somewhat jelly-like.

MFG has been recognized by disease specialists to occur most frequently in older fish. Economon suggests MFG to be present in 1 of 10,000 walleye 4.5 years or older. Economon, P. P., "Myofibrogranuloma, a Muscular Dystrophy-Like Anomaly of Walleye (*Stizostedion vitreum*), *Minnesota Dep. Nat. Resour. Fish Wildl. Spec. Publ.*, 113: 1–11 (1975). The mean total length at capture for walleye five years of age or older is generally greater than or equal to 500 mm.

The general nature of the muscle degeneration suggests MFG is of a hereditary nature. It has been suggested that MFG in walleye is apparently not sex-linked and that MFG represents a unique myopathy. Kelly, et al., "Chemical analysis of muscle from walleye (*Stizostedion vitreum vitreum*) with myofibrogranuloma, a chronic myopathy," Can. J. Fish. Aquat. Sci. 44: 1425–1431 (1987). Further, it has been demonstrated that the disease is most likely not infectious. Holloway, et al., "A myopathy in North Dakota walleye, *Stizostedion vitreum*," J. Fish Dis. 5: 527–530 (1982) Thus, due to MFG's probable genetic transmission, shipment of potentially diseased eggs is a concern of fishery biologists.

In addition, many lakes and reservoirs have increasingly used stocking as a management tool. For instance, at the Merritt Reservoir in north central Nebraska, the walleye population is maintained almost exclusively by stocking (Joel Klammer, Nebraska Game and Parks Commission, personal communication, Lincoln, Nebr. 68503-0370). Further, in 1990, over 6.2 million walleye fingerlings were stocked into Lake Sakakawea, North Dakota, to enhance the population. In lower Lake Oahe 221,250(1986), 299,500 (1987), 476,868 (1988) and 449,256 (1989) fingerling walleye were stocked. Fielder, D. G., "Evaluation of stocking walleye fry and fingerlings and factors affecting their success in lower Lake Oahe, South Dakota," North Am. J. Fish. Mgmt. 12: 336–345 (1992a); Fielder, D. G., "Relationship between walleye fingerling stocking density and recruitment in lower Lake Oahe, South Dakota," North Am. J. Fish. Mgmt. 12: 346–352 (1992b). Moreover, multiple years of almost complete year class failure and angler demand on the reservoirs have led to the increased stocking of walleye to enhance and even establish year classes.

MFG is of concern primarily in the Midwest, particularly in North and South Dakota, Minnesota, and Nebraska. Roe shipped from those states is sent throughout the country, wherever walleye is stocked for sport fishing. Therefore, a field test for this disease would be useful to remove diseased animals from the population and minimize the risk of spread via roe.

Present methods for detecting MFG can not be accomplished without filleting the fish since walleye with MFG generally show no external symptoms or abnormal behavior. Kelly et al. chemically analyzed 15 cases of MFG in adult walleye from 1975 to 1985 from seven lakes in southern Manitoba and northwestern Ontario and from Lake Sakakawea, North Dakota. Kelly, R. K., et al., "Chemical Analysis of Muscle From Walleye with Myofibrogranuloma, a Chronic Myopathy," *Can. J. Fish. Aquat. Sci.* 45: 1425–1431 (1987). The inorganic analysis of representative samples revealed elevations or depressions of ions which were consistent with those of extensively damaged muscle membrane systems. One of the greatest differences was seen in calcium levels which averaged 55 times normal in muscle lesions where excessive calcium deposition was demonstrable by histochemical staining with nuclear fast red. Id.

X-ray analysis has been utilized to show calcium deposits in the human kidney by Davidson, who stated that technicians are able to visualize various organs and systems radiographically because of differential absorption of X-rays, owing to differences in density of materials being examined. Davidson, A. J., "Excretory Urography", *Computed Tomography, Ultrasound and X-Ray: An Integrated Approach*, Masson Publishing U.S.A., Inc., New York, pp. 11–20 (1979). Thus, applicants hypothesized that muscles affected by MFG would have a higher density than normal muscle tissue, owing to the influx of calcium and subsequent calcification in advanced cases which could be detected with X-rays. The disadvantages of using X-rays, however, is that X-rays can be harmful to fish and would make subsequent genetic studies questionable. Therefore, there is a need in the art for a means of diagnosing MFG without filleting the fish or using X-rays.

Vascular biochemistry seemed the most likely choice since human muscular dystrophy is diagnosed with blood chemistry values. Many specific diseases, whether caused by bacteria, viruses or metabolic dysfunctions, are characterized by specific changes in the composition of the blood. Shell, E. W., "Chemical Composition of Blood of Smallmouth Bass," *Res. Rep. U.S. Fish Wildl.*, Serv. No. 57, U.S. Government Printing Office, Washington D.C. (1961). Diagnosis depends on the comparison of blood composition values of the animal with the suspected disease with blood composition of healthy animals of the same species.

Oser states that the normal range for calcium is narrow and small variations indicate pathology such as bone abnormalities and muscle tumors. Oser, B. L., *Hawk's Physiological Chemistry*, McGrawHill Book Company, New York, New York (1965). If calcium is regulated in the walleye, fish exhibiting MFG should have significantly different serum calcium levels than healthy walleye due to the 55-fold increase in muscle calcium associated with MFG shown by Kelly et al. in 1987. It was hypothesized that MFG-diseased walleye would exhibit relatively higher serum calcium concentrations than healthy walleye.

In 1993, it was discovered that there was a significant difference between mean serum calcium levels in spawning male and spawning female walleye. Serum calcium is higher in females due to the influence of estrogen which stimulates synthesis of yoke protein and an increase in protein bound plasma calcium. It was further found that the mean serum calcium levels of spawning male walleye was significantly different from the mean serum calcium levels of MFG-positive spawning male walleye. Similarly, there was a significant difference found between mean serum calcium levels of spawning female walleye and mean serum calcium levels of MFG-positive spawning female walleye. These elevations suggested that calcium was regulated in the walleye and that MFG was related to serum calcium levels. The calcium serum level test for MFG was not definitive, however, since there was an overlap of ranges between the healthy and MFG-positive spawning females and males. Therefore, it was determined that serum calcium levels, in and of themselves, could not be used to accurately diagnose MFG in walleye.

According to the invention, creatinine is another vascular parameter which potentially may be used to assess muscle degeneration. Phosphocreatine in muscle spontaneously cycles to creatinine. The quantity of end product, creatinine, is proportional to muscle mass and thus may be utilized in evaluating muscle mass. It was hypothesized that creatinine concentration in walleye serum would reflect these muscle mass-phosphocreatine/creatinine relationships. It was further hypothesized that since muscle mass decreases in MFG-afflicted walleye, albeit up to 20% in the most severe cases, that phosphocreatine may also decrease. A decrease in phosphocreatine means a reduction in the spontaneous cyclization to creatinine. If there is a reduction in creatinine levels in MFG-positive walleye, the values in the blood serum might reflect this.

Therefore, a primary objective of the present invention is to utilize a method for diagnosing MFG in walleye which is accurate and is not harmful to the fish. This invention has as its primary objective the fulfillment of this need.

Another objective of the present invention is to provide a method of diagnosing MFG in walleye which is more accurate than previously available methods.

Yet another objective of the present invention is to provide a method for diagnosing MFG which is easy to perform and cost effective.

The method and means of accomplishing these and further objectives of the invention will become apparent from the detailed description which follows hereinafter.

SUMMARY OF THE INVENTION

The present invention relates to a procedure for diagnosing myofibrogranuloma in walleye without impairing the fish for subsequent study or for use in spawning. The procedure involves the discriminant analysis of fish sex, total length, and a novel procedure measuring humoral concentrations of creatinine and calcium in blood serum to assess normal levels and the differences which are associated with and can be used as a marker for MFG. Tests are performed on walleye having a length greater than or equal to 500 mm and reveal that 88% of MFG-diseased walleye can be accurately identified.

DETAILED DESCRIPTION OF THE INVENTION

Figure 1:
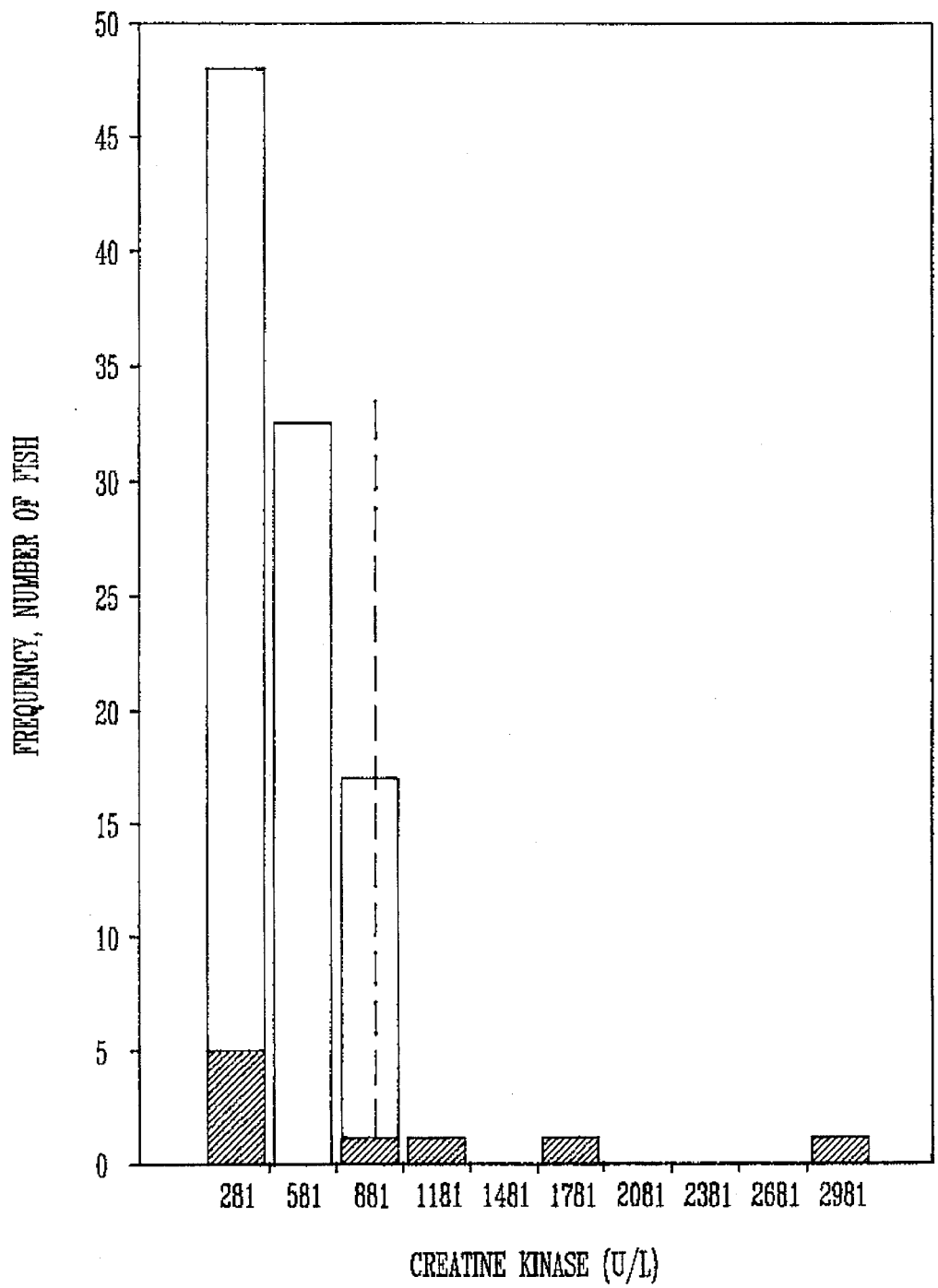
FIG. 1 is the frequency distribution of walleye serum creatine kinase values for MFG-positive fish from Lakes Sakakawea and Oahe and the Merritt Reservoir.

In accordance with the process of this invention, walleye having a total length of greater than or equal to 500 mm, since only walleye of at least this size (at least five years of age) show an incidence of MFG, are first collected. A blood sample is then collected via cardiac puncture, caudal artery, or other appropriate sites. Should cardiac puncture be used, an appropriate method uses a heparinized 21 gauge needle and 10 cc syringe. If samples are prepared in advance, they should be coagulated, clot milked and centrifuged within 24 hours of collection. Next, the samples are frozen until ready for analysis. The total length (mm), wet weight (grams), and sex (visual inspection) of the walleye are then determined. The fish may then be returned, unharmed, to their habitat.

The walleye blood is next analyzed for creatinine and calcium concentrations. Any methods used by those of ordinary skill in the art for making these determinations are suitable so long as they give accurate results. Finally, these values along with the walleyes' sex and length are analyzed using any accurate form of discriminant analysis.

Creatinine Determination

A preferred method for determining serum creatinine levels utilizes the principle that creatinine with alkaline picrate produces a color which is destroyed at acid pH. The difference in color chemistry measured at or near 500 μm before and after acidification is proportional to the creatinine concentration.

Reagents (1) Sodium hydroxide solution, 1.0N, Sigma Diagnostics. Catalogue No. 930-65;

(2) Acid reagent, mixture of sulfuric acid and acetic acid. Catalogue No. 555-2;

(3) Creatinine color reagent, picric acid, approximately 0.6%, sodium borate and surfactant. Catalogue No. 555-1;

(4) Creatinine standard, Creatinine, 3.0 mg/dL (0.26 mmol/L), in hydrochloric acid, 0.02N. Catalogue No. 925-3;

(5) Creatinine standard. Creatinine, 15 mg/dL (1.32 mmol/L), in hydrochloric acid, 0.02N. Catalogue No. 925-15.

Preparation:

Alkaline picrate solution is prepared by mixing 5 volumes of creatinine color reagent (Catalogue No. 555-1) with 1 volume of sodium hydroxide solution (Catalogue No. 930-65, e.g., 50 mL creatinine color reagent plus 10 mL sodium hydroxide solution).

Procedure

The described procedure is for a 3.4 mL reaction volume, requiring a 10–12 mm cuvet.

1) To cuvet labeled BLANK, add 0.3 mL water. To cuvet labeled STANDARD add 0.3 mL creatinine standard (Catalogue No. 925-3). To cuvet labeled TEST add 0.3 mL sample.

2) To all cuvets add 3.0 mL alkaline picrate solution. Mix and allow to stand at room temperature for 8–12 minutes.

3) Read and record absorbance (A) of STANDARD and TEST vs BLANK as reference at or near 500 nm. This is initial A.

4) To all cuvets add exactly 0.1 mL acid reagent (Catalogue No. 555-2). Mix immediately and thoroughly. Allow to stand 5 minutes at room temperature. NOTE: A precipitate may form upon addition of the acid reagent, but it dissolves after mixing.

5) Read and record absorbance (A) of STANDARD and TEST vs BLANK as reference at same wavelength used for the initial readings. This is FINAL A.

Calculations:

$$\text{Creatinine (mg/dL)} = \frac{\text{Initial } A_{Test} - \text{Final } A_{Test}}{\text{Initial } A_{Standard} - \text{Final } A_{Standard}} \times 3^*$$

*Concentration (mg/dL) of creatinine standard, Catalogue No. 925-3.

From: Sigma Chemical Company, 1988 Creatinine, Procedure No. 555, Sigma Diagnositics. St. Louis, MO. 8pp. Copyrighted.

Calcium Determination

A preferred method for determining serum calcium levels mixes the blood serum with murexide (ammonium purpurate) to form a red-colored calcium murexide complex which is in equilibrium with free calcium ions. Titrating the complex with EDTA chelates the free calcium ions, causing the murexide complex to release additional calcium ions to maintain the equilibrium. As the murexide ion/calcium murexide ratio increases there is a gradual shift of color from red to purple. The titration is followed photometrically at 620 nm to the endpoint, where the increase in optical density is maximum. The end point is reached when the murexide concentration is at its peak and all calcium ions have been bound by the chelating agent.

Reagents required:
 1) 0.05N sodium hydroxide. Dissolve 4 g sodium hydroxide in distilled water and qs to a volume of 2000 mL.
 2) 1.4N sodium chloride. Dissolve 81.8 g of sodium chloride in distilled water and qs to 1000 mL.
 3) 0.14N sodium chloride. Dilute 10 mL of the 1.4N sodium chloride to 100 ml with distilled water.
 4) 0.005M stock EDTA solution. Dissolve 1.85 g disodium dihydrogen ethylenediaminetetracetate in 100 mL 1.4N sodium chloride and add distilled water to make 1000 mL.
 5) Stock murexide. Dissolve 0.25 g of ammonium purpurate in 5 mL distilled water and 25 mL of 95% ethanol. Refrigerate in a brown bottle.
 6) Stock calcium standard 1%. Place 2.497 g of dry calcium carbonate into an evaporating dish. Dissolve in a minimal amount of 6N hydrochloric acid, and evaporate to dryness on a steam bath. Dissolve the residue (CaCl) in sufficient distilled water to make 100 mL.
 7) Working calcium standard. Dilute 1 mL of stock calcium standard to 100 mL with 1.4N sodium chloride. This solution contains 0.1 mg calcium per mL.

Procedure:
 1) Prepare the working murexide solution by adding the stock murexide solution to 100 mL of 0.05N sodium hydroxide until optical density is 0.48 to 0.39 in a 1 cm light path as compared to water at 620 nm.
 2) The titrant is prepared by mixing 18 volumes of the working murexide solution, 1 volume of 0.14N sodium chloride and 1 volume of stock EDTA solution.
 3) Place 0.25 mL of 0.14N sodium chloride solution in the blank cuvet, and equal quantities of fresh, nonhemolyzed serum and the working calcium standard in the test and standard cuvettes, respectively.
 4) Add 2.25 mL of working murexide solution and 0.5 mL of titrant to each cuvet, and mix.
 5) Set the blank cuvet to read a density of 0.500 on the photometer at 620 nm and read the test and standard cuvettes.
 6) Remove the cuvettes and add 0.25 mL of titrant to each, including the blank. Mix well.
 7) Rebalance the instrument to read 0.500 density at 620 nm with the blank and again read the test standard solutions.
 8) Repeat this procedure until the end point is passed and no further increase in density occurs.
 9) The end point is determined by preparing a plot of optical density versus titrant added on standard graph paper. A steep straight line is plotted, then there is a break, and a second straight line plateau is evident which intersects the first.

Calculation:
The ml required to give the end point is determined by finding the intersection of the two lines and reading the volume of titrant used at that point.

$$\text{mg calcium/100 mL serum} = \frac{\text{Volume of titrant required for serum}}{\text{Volume of titrant required for standard}} \times 10$$

Chemicals:
 1) sodium hydroxide
 2) sodium chloride
 3) disodium dihydrogen EDTA
 4) 95% Ethanol
 5) ammonium purpurate
 6) calcium carbonate
 7) 6N hydrochloric acid

Discriminant Analysis

After each separate parameter is analyzed, a discriminant analysis is carried out on diseased and healthy walleye in which the data for sex, length, creatinine and calcium are utilized. Discriminant analysis provides a mathematical rule, or discriminant function, for guessing which class (MFG-positive or healthy) a fish belongs to based on the knowledge of quantitative variables. A preferred discriminant analysis utilizes the DISCRIM procedure which is appropriate for approximately normal within-class distributions. SAS Institute Inc., *SAS User's Guide: Statistics, Version 5 Edition,* SAS Institute, Inc., Cary, N.C. (1985). Similar to the creatinine and calcium serum level determinations, other accurate discriminant analysis procedures may be utilized by those of ordinary skill in the art for practicing the present invention.

The following example is offered to illustrate experimentation we conducted wherein creatine kinase was rejected as a parameter to distinguish MFG-positive from healthy walleye. It also demonstrates that by using serum creatinine and calcium levels, MFG-positive walleye can be classified with great accuracy.

EXAMPLE

Field Collection of Walleye

Walleye were collected by trap nets (1.8×2.4 m) and experimental gill nets (1.8×75 m) with mesh sizes of 19, 25, 38, 51 and 64 mm bar measure. Merritt Reservoir walleye were sampled April 1991 and 1992. Sampling of Lake Oahe was carried out in April 1991 and August 1991. Lake Sakakawea was sampled summer 1990, May to September 1991 and May 1992. After the fish were captured, total length (mm), wet weight (grams) and sex (visual inspection) were recorded. Skeletal muscle samples of diseased fish and selected healthy walleye were collected and preserved in Bouin's solution or a 50:50 mixture of formaldehyde and 100% ethanol. Cardiac puncture was used to sample blood from live walleye using a heparinized 21 gauge needle and 10 cc syringe. Samples were coagulated, clot milked, and centrifuged within 24 hours of collection. Sera were collected in microcentrifuge tubes, frozen on dry ice for transport to the laboratory and placed in a $-80°$ C. freezer until analyzed.

Serum Biochemical Tests

Creatine kinase (CK) was determined by Sigma's protocol for the quantitative, kinetic determination of creatine kinase activity in serum or plasma read in a spectrophotometer at 340 nm. Sigma Diagnostics, *Creatine Kinase Procedure No. 47-UV*, St. Louis, Mo. (1989). A Bausch and Lomb Spectronic 20, matched cuvets (12 mm) and voltage regulator were utilized in determining CK activity. Bausch and Lomb Spectronic 20's are wide-bandwidth instruments which do not emit truly monochromatic light at 340 nm. The absorbance readings of these instruments, while reproducible are not necessarily "correct". Therefore, readings from the Spectronic 20 were adjusted to obtain the "correct" absorbance values prior to use in calculations. Sigma's procedure number 30-UV was used as a simple calibration procedure for adjusting the absorbance readings of our wide-bandwidth instrument. The determinations were carried out at $30°$ C.$\pm$one degree with the use of a constant temperature waterbath. The reagent and sample were incubated at $30°$ for three minutes. Absorbance readings were then taken at 30 second intervals for two minutes to assure linearity. Creatine kinase activity (U/L) was then determined by use of the manufacturer's formula. Dilutions of lyophilized rabbit muscle CK (2100 U/L) were used as controls for testing procedures. Some assays did not proceed in a linear fashion due to hemolysis, which caused high levels of adenylate kinase, ATP and glucose-6-phosphate to be released from red cells affecting the reaction. These assays were not considered in the analysis. A frequency distribution of the data was made and a graphical test for normality (Gaussian distribution) carried out. The data were found not to follow a Gaussian distribution, therefore, $\pm 2$ SD from the mean is not an acceptable method to express the health range of CK. Creatine kinase values were analyzed by a procedure utilized on non-normally distributed serum values of dogs. Brunden et al, "A General Method of Determining Normal Ranges Applied to Blood Values for Dogs," *Am. J. Clin. Path.*, 53: 332–339 (1970). Sommerville's table was used to obtain the value of m (a table value that satisfies a formulated inequality) which was utilized to calculate the upper tolerance limit. Sommerville, P. N., "Tables for Obtaining Non-Parametric Tolerance Limits," *Ann. Math. Stat.*, 29: 599–601.

Creatinine was evaluated in the serum of MFG-positive walleye using the Sigma Diagnostic's protocol.

The procedure to determine the concentration of calcium (Ca) in serum was modified from Fales (1953) by Oser (1965). The latter protocol was used. The volume of serum and reagents were halved due to the small amount of serum available for some fish. A Ca standard (0.1 mg/ml) was utilized. Oser suggested setting the spectrophotometer at 0.50 density with the blank before reading the standard and test. In the text, Oser refers to balancing the instrument at 0.50 absorbance and reading optical density, however, he plots % transmittance. We elected to follow Fales (1953) original procedure and set the spectrophotometer at 50% transmittance, not 0.50 absorbance. The light sensitive stock murexide solution was refrigerated in a brown bottle. The working murexide and titrant were mixed prior to each set of determinations, kept in brown bottles and used within 1.5 hours. Because of light sensitivity the cuvets were kept in a dark cardboard box to avoid exposure to room light.

The determination was based on the titration of Ca with disodium dihydrogen ethylene-diaminetetraacetic acid (EDTA). The titration was followed colorimetrically at 620 nm using a Bausch and Lomb Spectronic 20. Matched cuvets (12 mm) and voltage regulator standardized the procedure. Calculations were carried out as described by Oser (1965). A t-test was utilized to compare the mean serum calcium levels of healthy male and female walleye. Due to small sample size and differences in variance, mean serum Ca levels of healthy male and female spawning walleye were compared to mean serum Ca values of MFG-positive fish of the same sex using an unequal variance t-test. Sokal, R. R., and F. J. Rolf, *Biometry*, W. H. Freemand and Co., New York, N.Y. (1981). The critical level of significance utilized was also different for tests between male and female walleye ($P<0.05$) and between MFG-positive and healthy male walleye and MFG-positive and healthy female walleye ($P<0.10$). Different levels were used because of the numbers of MFG-positive fish (four females and six males).

Discriminant Analysis

After each separate parameter was analyzed, a discriminant analysis was carried out on diseased and healthy walleye in which the data for sex, length, creatine kinase, creatinine, and calcium were available (28 total; 6 disease and 22 healthy). The procedure utilized was the DISCRIM procedure (SAS Institute Inc. 1985) which is appropriate for approximately normal within-class distributions. However, before the DISCRIM procedure was carried out, a stepwise discriminant analysis, STEPDISC procedure, (SAS Institute Inc. 1985) was performed to select a subset of variables for use in the DISCRIM procedure. Of the variables stated above (sex, length, creatine kinase, creatinine and calcium) none could be removed by STEPDISC based on: (1) the significance level of an F-test from an analysis of covariance, where the variables already chosen act as covariates and variable under consideration is the dependent variable or (2) the squared partial correlation for predicting the variable under consideration from the class variable. This second criterion allows for control of the effects of variables already selected for the model. Thus, all variables were included in the discriminant analysis. Another discriminant analysis using sex, length, creatinine and calcium was carried out. This enabled us to increase the number of walleye in the analysis to 33 (23 healthy and 10 diseased).

Results

Creatine kinase values of 91 healthy walleye ranged from 131 to 951 U/L. FIG. 1 represents the frequency distribution of CK values for walleye from lakes Sakakawea, Oahe, and Merritt Reservoir. Our desired upper 90—90 tolerance limit (i.e., 90% probability of covering 90% of the population) was found to be the 95th ranked variate which had a value of 885 U/L CK activity (this is represented by the dashed line on FIG. 1 in which MFG-positive walleye are represented in black). According to the procedure by Brunden et al. (1970), on average (or more often), all CK values less than or equal to 885 U/L include 90% of the population of healthy walleye. Three (1082, 1902 and 2952 U/L) of the nine MFG-positive CK values (Table 5 and FIG. 1) fell above the calculated upper limit, one value (787 U/L) was close to the established upper limit and five values (197, 295, 328, 328 and 349 U/L) were below the established upper tolerance limit.

Creatinine values for MFG-positive fish are presented in Table 1. The mean creatinine value for all MFG-positive walleye (Merritt and Lake Sakakawea) was compared to the mean value of 45 healthy walleye and no significant difference (P>0.10) was found between the mean creatinine values of healthy (0.283 mg/dl) and MFG-positive walleye (0.34 mg/dl).

TABLE 1

Mean, standard deviation and range of creatinine in mg/dl for MFG-positive walleye.

| Location | Sample size | Mean mg/dl | +/− SD | Range mg/dl |
|---|---|---|---|---|
| Lake Sakakawea | n = 7 | 0.327 | .167 | .15–.59 |
| Merritt Reservoir | n = 7 | 0.353 | .110 | .24–.51 |
| Combined | n = 14 | 0.340 | .137 | .15–.59 |

Figure 2:
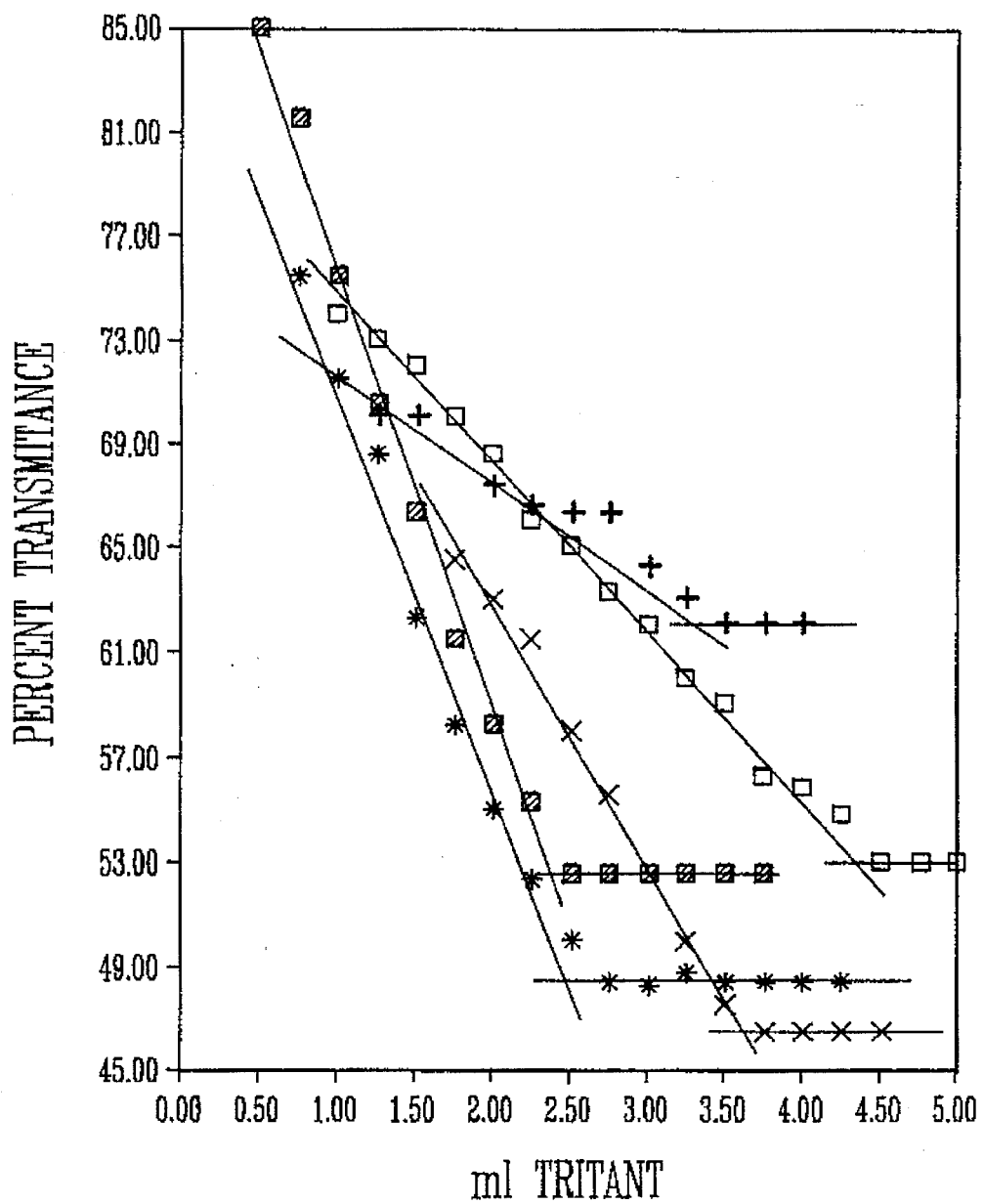
FIG. 2 sets forth selected calcium titration curves of spawning walleye (Standard=0.1 mg Ca/ml; NB201 - healthy female; 0066 - healthy male; 0043 - MFG-positive male).

Selected calcium titration curves [standard, spawning female (NB201), spawning male (0066), MFG-positive spawning female (0043) and MFG-positive spawning male (0252)] are shown in FIG. 2. The titration curves show a steep straight line followed by the plateau at the bottom of the curve; their intersection indicates the amount of titrant (EDTA) required to titrate serum Ca.

Table 2 shows serum Ca values of: (1) spawning female walleye, (2) spawning male walleye, (3) MFG-positive spawning male walleye, and (4) MFG-positive spawning female walleye. A significant difference $t_s=6.81$, df=36, p<0.05) was found between mean serum Ca levels of spawning male ($\bar{X}=11.68$ mg/100 ml serum) and spawning female walleye ($\bar{X}=15.36$ mg/100 ml serum). Mean serum Ca levels of spawning male walleye ($\bar{X}=11.68$ mg/100 ml serum) differed significantly ($t_s=2.088$, df=17,5, p<0.10) from mean serum levels of MFG-positive spawning male walleye ($\bar{X}=13.62$ mg/100 ml serum). A significant difference ($t_s=2.561$, df=19,3, p<0.10) was found between mean serum Ca levels of healthy spawning female walleye ($\bar{X}=15.36$ mg/100 ml serum) and MFG-positive spawning female walleye ($\bar{X}=20.20$ mg/100 ml serum).

TABLE 2

Serum Ca (mg/100 ml) of spawning reservoir walleye (healthy male and female) with values of MFG-positive fish (male and female).

| | Sample Size | Mean | +/− SD | Range | Mean Age |
|---|---|---|---|---|---|
| Healthy female | 20 | 15.36 | 1.78 | 11.90–19.47 | 8.7 |
| Healthy male | 18 | 11.68 | 1.51 | 9.09–14.61 | 8.6 |
| MFG-Positive male | 6 | 13.62 | 2.10 | 11.49–16.80 | 8.8 |
| MFG-positive female | 4 | 20.20 | 3.70 | 17.12–25.35 | 11.5 |

Discriminant Analysis

The descriptive statistics from the discriminant analysis are presented in Table 3. Twenty-two healthy walleye and six MFG-positive walleye were included in the analysis. Five of six (83%) diseased fish were correctly classified as MFG-positive and 20 of 22 (90%) healthy walleye were correctly classified. Three of 28 fish (11%) were misclassified using the variables sex, length, creatine kinase, creatinine and calcium. Table 4 presents descriptive statistics of the analysis which did not include creatine kinase as a variable. Twenty-three healthy and ten MFG-positive walleye were utilized in the analysis. Eight of ten (80%) diseased fish were correctly classified as MFG-positive and 21 of 23 (91%) healthy walleye were correctly classified. Four of the total 33 fish (12%) were misclassified using the variables sex, length, creatinine, and calcium.

TABLE 3

Descriptive statistics of discriminant analysis using the variables sex, length, creatinine, calcium and creatine kinase.

| Variable | N | Sum | Mean | Variance | STD Dev |
|---|---|---|---|---|---|
| Total-sample | | | | | |
| sex | 28 | 12 | 0.43 | 0.25 | 0.50 |
| length | 28 | 17051 | 609 | 5127 | 71.60 |
| creatinine* | 28 | 6.82 | 0.24 | 0.026 | 0.16 |
| calcium | 28 | 391 | 13.98 | 13.3 | 3.64 |
| creatine kinase | 28 | 12590 | 450 | 54177 | 233 |
| Healthy-sample | | | | | |
| sex | 22 | 9 | 0.40 | 0.25 | 0.50 |
| length | 22 | 13189 | 600 | 4719 | 68.69 |
| creatinine* | 22 | 5.10 | 0.23 | 0.026 | 0.16 |
| calcium | 22 | 286 | 13.01 | 7.0 | 2.64 |
| creatine kinase | 22 | 9519 | 432 | 39963 | 200 |
| MFG-positive-sample | | | | | |
| sex | 6 | 3 | 0.50 | 0.30 | 0.55 |
| length | 6 | 3862 | 643 | 6027 | 77.63 |
| creatinine* | 6 | 1.72 | 0.29 | 0.025 | 0.16 |
| calcium | 6 | 105 | 17.55 | 23.0 | 4.80 |
| creatine kinase | 6 | 3071 | 512 | 118806 | 344 |

TABLE 4

Descriptive statistics of discriminant analysis using the variables sex, length, creatinine and calcium.

| Variable | N | Sum | Mean | Variance | STD Dev |
|---|---|---|---|---|---|
| Total-sample | | | | | |
| sex | 33 | 13 | 0.39 | 0.25 | 0.50 |
| length | 33 | 20092 | 609 | 4950 | 70.36 |
| creatinine* | 33 | 8.71 | 0.26 | 0.026 | 0.16 |
| calcium | 33 | 464 | 14.06 | 11.9 | 3.45 |
| Healthy-sample | | | | | |
| sex | 23 | 9 | 0.39 | 0.25 | 0.50 |
| length | 23 | 13754 | 598 | 4556 | 67.50 |
| creatinine* | 23 | 5.58 | 0.24 | 0.028 | 0.17 |
| calcium | 23 | 299 | 12.99 | 6.70 | 2.58 |
| MFG-positive-sample | | | | | |
| sex | 10 | 4 | 0.40 | 0.27 | 0.52 |
| length | 10 | 6338 | 634 | 5472 | 74.00 |
| creatinine* | 10 | 3.13 | 0.31 | 0.020 | 0.14 |
| calcium | 10 | 165 | 16.55 | 16.2 | 4.03 |

Only three of nine MFG-positive walleye showed elevated CK levels (i.e. above the 90—90 tolerance interval of 885 U/L). This suggests that the degree of muscle degeneration in most MFG-positive specimens was not great enough ($\leq 20\%$ by visual inspection in most severe cases) to affect circulating CK levels. The muscle degeneration may have been progressing at such a slow rate that the elevations may have leveled out and only by sampling when the muscle was actively degenerating would an elevation of CK be detected. Even then elevated CK levels may not be detected. It may be necessary to use a micromethod at sites close to degenerating muscles because of dilution in the circulating blood. Another possible explanation may be a result of the activity patterns of the walleye. Economon (1978) suggests walleye are passive swimmers and are not even very active when captured by hook and line. Thus, CK may be present in low levels in walleye due to the fishes behavior (i.e., low activity hence little ATP required). Thus only a small amount of CK may be needed to phosphorylate ADP by dephosphorylating phosphocreatine to form the needed ATP.

Values of creatinine were obtained for 14 MFG-positive walleye (Table 1). In man, when muscle degenerates due to paralysis or muscular dystrophy the creatinine content of the blood falls (Emery 1988). The MFG-positive creatinine values were not significantly different than the mean value of the 45 healthy walleye and suggest creatinine may not be the variable to use in diagnosing muscle degeneration in walleye. The filtration of creatinine by the non-diseased kidney may be so precise that the small loss of muscle mass ($\leq 20\%$) does not affect the humoral systemic level of creatinine in MFG-positive walleye.

Conclusion

No single blood parameter examined seemed to clearly differentiate healthy walleye from MFG-positive walleye. Discriminant analysis allowed for the use of selected blood parameters, sex and length as variables. Because multiple parameters for some walleye were measured, a statistical procedure was utilized to classify fish as healthy or MFG-positive on the basis of the numeric variables (i.e. sex, length, creatine kinase, creatinine and calcium). All fish were not able to be correctly classified using these variables, but 89% (25 of 28 walleye) were classified correctly using all variables and 88% (29 of 33 walleye) were correctly classified without creatine kinase. If this procedure were utilized by fish managers, it would not "catch" all diseased fish. In the analysis using all variables as criteria 83% (5 of 6) of the diseased fish were recognized. Eighty-percent (8 of 10) of the diseased individuals were recognized in the analysis without creatine kinase as a variable. Discriminant analysis seems to provide a means of distinguishing most diseased walleye correctly. Perhaps, with an increased sample of diseased individuals, discriminant analysis would be more effective in distinguishing healthy walleye and MFG-positive walleye. Discriminant analysis would require a tagging procedure because data collection and analysis would take more time than spawning operations would allow. Thus, walleye classified as

TABLE 5

Descriptive values for serum parameters ascertained for MFG-positive walleye.
(Cre = creatinine mg/dl; Ca = calcium mg/100 ml; Ck = creatine kinases U/L).

| Fish # | Lake | Sex | Cre | Ca | CK | Time |
|---|---|---|---|---|---|---|
| 0043 | Sak! | F@ | 0.18 | 20.33 | 787 | SP# |
| 0063 | Sak | M& | 0.40 | 13.83 | NV | SP |
| 0065 | Sak | M | 0.15 | 15.31 | 1082 | SP |
| 0139 | Sak | F | 0.18 | 17.12 | NV | SP |
| 0252 | Sak | M | 0.47 | 16.80 | NV | SP |
| 0278 | Sak | F | 0.59 | 17.94 | 197 | SP |
| 1221 | Sak | M | 0.32 | 12.23 | 295 | PS+ |
| NB7 | Mer* | M | NV% | NV | 1902 | SP |
| NB13 | Mer | M | 0.30 | NV | NV | SP |
| NB18 | Mer | M | 0.36 | 12.40 | NV | SP |
| NB40 | Mer | M | 0.51 | NV | NV | SP |
| NB43 | Mer | M | 0.50 | NV | 2952 | SP |
| NB212 | Mer | M | 0.26 | 11.49 | 328 | SP |
| NB214 | Mer | M | 0.30 | 11.88 | 328 | SP |
| NB235 | Mer | F | 0.24 | 25.35 | 349 | SP |

! Sak = Lake Sakakawea
* Mer = Merritt Reservoir
@ F = Female
& M = Male
SP = Spawning
+ PS = Post spawn
% NV = No value due to the volume of serum collected MFG-positive could be recognized and subsequently removed when recaptured.

One of the greatest difficulties in studying MFG may be its incidence in adult walleye (one of 15 to 20 fish sampled). These walleye are the brood stock for future generations and fish managers are hesitant to allow researchers access to these individuals. Discriminant analysis will allow for the majority of the brood fish to be returned to the population being examined while most walleye with advanced cases of MFG can be removed for further study.

The examples shown above are not intended to limit the described invention in any manner but are included for demonstrative purposes only.

It is therefore seen that the present invention accomplishes at least all of its stated objectives.

What is claimed is:

1. A method of detecting myofibrogranuloma (MFG) in walleye, wherein the walleye is greater than or equal to 500 mm total length, comprising:

determining the serum creatinine value in a walleye;

determining the serum calcium value in the walleye; and performing a discriminant analysis utilizing the serum creatinine value and serum calcium value as quantitative variables.

2. The method of claim 1 wherein the mean serum creatinine level for MFG-positive walleye is 0.34 mg/dl.

3. The method of claim 1 wherein the serum calcium level for MFG-positive male walleye is within the range of 11.49–16.80 mg/100 ml and the serum calcium level for MFG-positive female walleye is within the range of 17.12–25.35 mg/100 ml.

4. The method of claim 3 wherein the mean serum calcium level for MFG-positive male walleye is 13.62 mg/100 ml and the mean serum calcium level for MFG-positive female walleye is 20.20 mg/100 ml.

5. The method of claim 1 wherein the discriminant analysis uses the variables sex, length, creatinine and calcium.

6. The method of claim 1 wherein about 88% of MFG-positive walleye are recognized.

7. An improved method for detecting myofibrogranuloma (MFG) in walleye comprising:

measuring the serum calcium level in a walleye;

measuring the serum creatinine level in the walleye;

evaluating the serum calcium level and serum creatinine level in conjunction with the mean serum calcium and creatinine levels from MFG-positive walleye and healthy walleye using discriminant analysis.

8. The improved method of claim 7 wherein the walleye is greater than or equal to 500 mm in total length.

9. The improved method of claim 7 wherein the mean serum calcium level for MFG-positive male walleye is 13.62 mg/100 ml and the mean serum calcium level for MFG-positive female walleye is 20.20 mg/100 ml.

10. The improved method of claim 7 wherein the mean serum creatinine level for MFG-positive walleye is 0.34 mg/dl.

11. The improved method of claim 7 wherein the mean serum calcium level for healthy male walleye is 11.68 mg/100 ml and the mean serum calcium level for healthy female walleye is 15.36 mg/100 ml.

12. The improved method of claim 7 wherein the mean serum creatinine level for healthy walleye is 0.283 mg/dl.

* * * * *